United States Patent [19]

Cook et al.

[11] Patent Number: 5,585,400
[45] Date of Patent: Dec. 17, 1996

[54] METHODS OF ATTENUATING THE ALLERGIC RESPONSE IN ANIMALS

[75] Inventors: Mark E. Cook; Ellen B. Cook; James L. Stahl, all of Madison; Frank M. Graziano, Oregon; Michael W. Pariza, Madison, all of Wis.

[73] Assignee: Wisconsin Alumni Research Foundation, Madison, Wis.

[21] Appl. No.: 607,498

[22] Filed: Feb. 27, 1996

[51] Int. Cl.$^6$ .................................................. A61K 31/20
[52] U.S. Cl. .............................................. 514/560
[58] Field of Search ............................... 514/560

[56] References Cited

U.S. PATENT DOCUMENTS

| | | | |
|---|---|---|---|
| 4,386,072 | 5/1983 | Horrobin et al. | 514/552 |
| 4,603,142 | 7/1986 | Burger et al. | 514/456 |
| 4,868,001 | 9/1989 | Maruta | 426/623 |
| 5,017,614 | 5/1991 | Pariza et al. | 514/558 |
| 5,070,104 | 12/1991 | Pariza et al. | 514/549 |
| 5,162,337 | 11/1992 | Elbrecht et al. | 514/300 |

OTHER PUBLICATIONS

Biosis Abst. No. 94064501, Iwamoto et al., Cancer Lett. 64(1), pp. 17–22 1992.
Passwater, "Evening Primrose Oil", published by Keats Publishing, Inc., pp. 3–7 1981.
Y. L. Ha; N. K. Grimm and M. W. Pariza, *Carcinogenesis*, vol. 8, No. 12, pp. 1881–1887 (1987).
Y. L. Ha; N. K. Grimm and M. W. Pariza, J. Agric. Food Chem., vol. 37, No. 1, pp. 75–81 (1987).
M. W. Pariza, Food Research Institute 1988 Annual Fall Meeting, Oct. 12, 1988.
The Merck Index, Tenth Edition (1983), p. 790.
The Merck Veterinary Manual, Fifth Edition (1979), pp. 1340–1343 and 1374 and 1379.
Hodge L., Peat J K, Salome C. "Increased consumption of polysaturated oils may be a cause of increased prevalence of child asthma." Australian & NZ J Med 24(6):727, 1994 Dec.
Thien F., Woods R., Walters E H, "Asthma spoils from polyunsaturated oils," Australian & NZ J Med 25(1):63–4, 1995 Feb.

*Primary Examiner*—Raymond Henley, III
*Attorney, Agent, or Firm*—Quarles & Brady

[57] ABSTRACT

Methods of treating animals to prevent or treat the adverse effects of type I or $I_gE$ mediated hypersensitivity in the animal consist of administering to the animal a safe and effective amount of a conjugated linoleic acid (CLA) or a substance which is converted in the animal into CLA. Methods of increasing the white blood cell count in a mammal and preserving white blood cells with CLA also are disclosed.

6 Claims, 1 Drawing Sheet

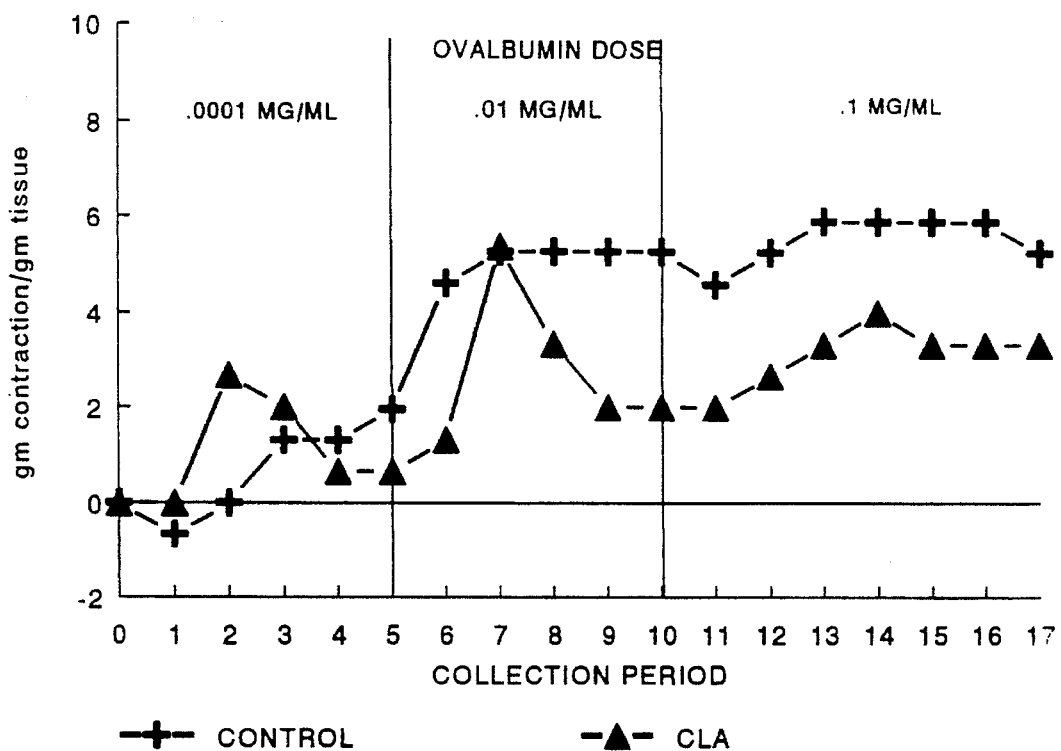
FIGURE 1 ANTIGEN CHALLENGE OF GUINEA PIG TRACHEAE: CONTRACTION
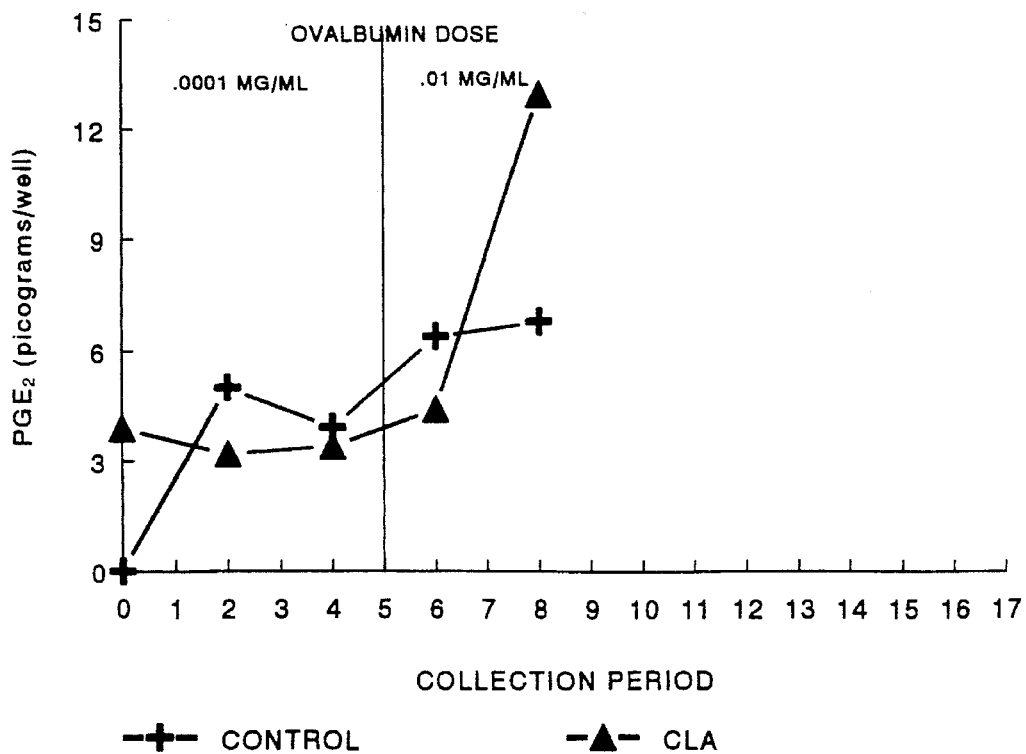
FIGURE 2 ANTIGEN CHALLENGE OF GUINEA PIG TRACHEAE: $PGE_2$ RELEASE

METHODS OF ATTENUATING THE ALLERGIC RESPONSE IN ANIMALS

FIELD OF THE INVENTION

The present application generally relates to methods of treating animals, including humans. More particularly, it relates to methods of treating animals to attenuate the allergic response in said animals. It is known that attenuating the allergic response in an animal can be beneficial in various conditions, such as asthma.

BACKGROUND OF THE INVENTION

Allergy is a term commonly used to describe several forms of hypersensitivity. Hypersensitivity usually is classified into four types referred to by the Roman numerals I–IV. Types I to III hypersensitivities are mediated by antibodies and type IV is believed to be mediated by lymphocytes.

Asthma, hay fever, and eczema are considered to be of the type I form of hypersensitivity that is mediated by $I_gE$ antibodies and it is present in a significant percentage of humans. There is a general consensus that the mortality rates for asthma in much of the developed world have been increasing for the past 10–15 years. This increase has occurred despite an improved information base regarding diagnosis and management as well as the development of novel and more effective therapeutic modalities. Several explanations have been proposed for this increase, including a statistical artifact based on a change in the coding criteria for asthma from the International Classification of Diseases Version 8 to Version 9, worsened pollution, delays in seeking medical help, behavioral changes, deficits in asthma education of both patients and primary care providers, toxicity of beta agonists, and noncompliance with medications. It has been suggested that a change in our eating habits may contribute as well. The emphasis on reducing the intake of saturated fats and cholesterol has resulted in greater consumption of polyunsaturated fats and a consequent doubling of the percentage of the polyunsaturated linoleic acid in body fat. The only published results exploring the effects of dietary components on asthma show a positive effect of dietary fish oil on asthma and other inflammatory diseases.

The $I_gE$ mediated hypersensitivity or type I hypersensitivity also is sometimes referred to as "immediate hypersensitivity" because its effects are recognizable within minutes on rechallenge with antigen. It is dependent upon the binding of $I_gE$ antibodies to their receptors on mast cells and basophils. Cross-linking of the bound antibodies by antigen leads to the degranulation of the mast cells and basophils and to the synthesis of biologically active substances, which together with mediators, such as histamine, released from granules can cause an injurious form of inflammatory response.

It is not known with certainty what activates the mast cells and basophils to degranulate and to release the mediators from the granules. However, the degranulation or activation results in the release of prostaglandins and leukotrienes that are believed to be responsible for the clinical manifestations of the allergic reactions. Some of the mediators act upon other cells, such as eosinophils, neutrophils, monocytes, and lymphocytes to produce other substances which attack or are toxic to tissue and can lead to further clinical manifestations. Whatever the mechanism, the net result of a type I hypersensitivity attack can be very serious and even can be death.

It obviously would be advantageous to have both methods of attenuating the allergic response by preventing or inhibiting the adverse effects of type I hypersensitivity in an animal and methods for treating or alleviating such adverse effects.

BRIEF SUMMARY OF THE INVENTION

It is one object of the present invention to disclose a method of preventing or inhibiting the adverse effects of type I or $I_gE$ mediated hypersensitivity in an animal.

It also is an object of the present invention to disclose a method for treating or alleviating the adverse effects caused by a type I or $I_gE$ mediated hypersensivity in animals, including humans.

It also is an object to disclose methods of preserving white blood cells using conjugated linoleic acids (CLA).

We have discovered that a method comprising the administration to an animal of safe and effective amounts of the conjugated linoleic acids 9,11-octadecadienoic acid and 10,12-octadecadienoic acid (CLA) or a substance that is converted in the animal to CLA can inhibit or prevent the adverse effects of type I or $I_gE$ mediated hypersensitivity in the animal.

We also have discovered that a method comprising the administration of CLA to an animal experiencing the adverse effects of type I or $I_gE$ mediated hypersensitivity can beneficially treat or alleviate those adverse effects.

Finally, we also have discovered a method of preserving white blood cells with CLA.

It will be apparent to those skilled in the art that the aforementioned objects and other advantages may be achieved by the practice of the present invention.

BRIEF DESCRIPTION OF THE DRAWINGS

In the drawings:

FIG. 1 is a graph showing the antigen dose response curves of CLA versus a control; and FIG. 2 is a graph showing Proctoglandin E2 release from guinea pig tracheae treated with CLA and controls.

DESCRIPTION OF THE PREFERRED EMBODIMENT

In the preferred method of the present invention for inhibiting or preventing the adverse effects of a type I or $I_gE$ mediated hypersensitivity in an animal, a safe and effective amount of conjugated linoleic acid (CLA) or a substance that is converted to CLA in the animal is administered to the animal, including a human, to inhibit or prevent the onset of those adverse effects.

In the preferred method of the present invention for beneficially treating or alleviating the adverse effects of type I or $I_gE$ hypersensitivity in an animal, a safe and effective amount of a conjugated linoleic acid (CLA) or a substance that is converted to CLA in the animal is administered to an animal, including a human, which is experiencing such adverse effects.

The mechanism by which type I hypersensitivity causes its adverse effects in animals is not known. However, it is possible that viral infections are causing the type I hypersensitivity or making animals susceptible to it and that the CLA is in some way interfering with the viral initiated response.

Since CLA is a natural food ingredient and it is relatively non-toxic, the amounts which can be administered in the methods of the invention are not critical as long as they are enough to be effective. However, because of the differences in size and susceptibility of animals, including humans, the amounts which are safe and effective can vary considerably.

In the preferred method for preserving white blood cells, a safe and effective amount of CLA is mixed with the white blood cells to be preserved. The amount of CLA employed will normally be about 0.1% to about 1% by weight of the white blood cells.

The term CLA as used herein includes the free conjugated linoleic acids such as 9,11-octadecadienoic acid and 10,12-octadecadienoic acid; the active isomers of CLA; non-toxic salts thereof; active esters and other active chemical derivatives thereof; and mixtures thereof.

The free conjugated linoleic acids (CLA) have been previously isolated from fried meats and described as anti-carcinogen by Y. L. Ha, N. K. Grimm and M. W. Pariza, in Carcinogenesis Vol. 8, No. 12, pp. 1881–1887 (1987). Since then, they have been found in some processed cheese products (Y. L. Ha, N. K. Grimm and M. W. Pariza, in J. Agric. Food Chem., Vol. 37, No. 1, pp. 75–81 (1987)).

The free acid forms of the CLA may be prepared by isomerizing linoleic acid. The non-toxic salts of the free CLA acids may be made by reacting the free acids with a nontoxic base. Natural CLA may also be prepared from linoleic acid by the action of $W^{12}$-cis, $W^{11}$-transisomerase from a harmless microorganism such as the Rumen bacterium *Butyrivibrio fibrisolvens*. Harmless microorganisms in the intestinal tracts of rats and other monogastric animals may also convert linoleic acid to CLA (S. F. Chin, W. Liu, K. Albright and M. W. Pariza, 1992, FASEB J.6:Abstract #2665).

The CLA may also be prepared by use of the bacteria of which will synthesize CLA from linoleic acid. The resulting CLA is both stable and easily extracted from the fermentation broth.

Another convenient way of supplying CLA is by use of a milk naturally enriched with CLA. The milk can be prepared by adding a source of free linoleic acid and a harmless bacteria to milk and incubating the mixture for about 1 hour at 37° C. or until the linoleic acid is converted into CLA.

The CLA obtained by the practice of the described methods of preparation contains one or more of the 9,11-octadecadienoic acids and/or 10,12-octadecadienoic acids and active isomers thereof. It may be free or bound chemically through ester linkages. The CLA is heat stable and can be used as is, or dried and powdered. The CLA is readily converted into a non-toxic salt, such as the sodium or potassium salt, by reacting chemically equivalent amounts of the free acid with an alkali hydroxide at a pH of about 8 to 9.

Theoretically, 8 possible geometric isomers of 9,11- and 10,12-octadecadienoic acid (c9,c11; c9,t11; t9,c11; t9,t11; c10,c12; c10,t12; t10,c12 and t10,t12) would form from the isomerization of c9,c12-octadecadienoic acid. As a result of the isomerization, only four isomers (c9,c11; c9,t11; t10, c12; and c10,c12) would be expected. However, of the four isomers, c9,t11- and t10,c12- isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9,c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

The methods of the present invention can take several embodiments. In one embodiment, the CLA to be administered is simply added to the animal's or human's food. In another embodiment, the CLA can be administered to an animal in a pharmaceutical or veterinary dosage form containing a safe and effective dose of the CLA. In a third embodiment, the animal can be fed a safe amount of a substance such as free linoleic acid which can be formed into CLA in situ in the animal or human.

The CLA and its non-toxic derivatives, such as the non-toxic salts, in addition to being added to an animal's food or formed in situ can be administered in the form of pharmaceutical or veterinary compositions, such as tablets, capsules, solutions or emulsions to the animal or the humans. The exact amount to be administered, of course, depends upon the form of CLA employed, the route of administration, and the nature of the animal's or human's condition. Generally, the amount employed of CLA and its non-toxic salts employed as a pharmaceutical will range from about one part per million (ppm) to about 10,000 ppm of CLA in the animal's or human's diet. However, the upper limit of the amount to be employed is not critical because CLA is relatively non-toxic and it is a normal constituent of the human diet (including human breast milk). The amounts to be added to a conventional animal feed or human's food as an additive can range from 0.01% to 2.0% or more by weight of the animal's or human's food.

The preferred pharmaceutical and veterinary compositions of CLA contain the non-toxic sodium or potassium salt of CLA in combination with a pharmaceutical diluent. When the compositions are solutions or suspensions intended for external or oral administration, the diluent will be one or more liquid diluents. When the product is a tablet or capsule, a conventional diluent can be employed. When the compositions are solutions or suspensions intended for parenteral administration the preferred diluent will be Sterile Water for Injection U.S.P.

The following examples further illustrate the practice of the present invention.

EXAMPLE 1

It is recognized that the guinea pig is a useful model in the pre-clinical evaluation of substances for use in the treatment of asthma (M. G. Compos and M. K. Church, Clinical and Experimental Allergy, 1992, Volume 22, pages 665–666). Therefore, a guinea pig model was used to measure the effect of dietary CLA (conjugated linoleic acid) on the allergic response.

Guinea pigs were fed 0.25% CLA or control diets for two weeks, then immunized with ovalbumin on weeks two and three for hyperimmunization. The guinea pigs were euthanized, and tracheae were collected and used in a superfusion model system to determine if feeding CLA had any effect on allergen-induced tracheal contraction. (The superfusion model system consists of connecting the excised tissue to a polygraph and measuring contraction by the offset of the polygraph.) It was observed that tracheae from guinea pigs fed CLA were more stable in the superfusion system than tracheae of control-fed guinea pigs (that is, needing fewer corrections to return the tissue to baseline tension during equilibration). When allergen was infused over the guinea pig tracheae, after one hour of equilibration, less tracheal contraction was observed in the tissue of the CLA-fed animals. The reduced tracheal contraction corresponded to an increased Prostaglandin $E_2$ release as measured by enzyme-linked immunosorbent assay. These results are shown on FIGS. 1 and 2. Histamine release was not affected by diet.

EXAMPLE 2

It was observed in animals fed CLA that their White Blood Cell (WBC) counts were increased to $3.5 \times 10^6$/ml±0.6 as compared to control animals which had WBC counts of $2.4 \times 10^6$/ml±0.3 (mean +/− SEM). Thus, feeding CLA can be used as a method to increase WBC counts in mammals.

EXAMPLE 3

CLA (1% by weight) is added to isolated human white blood cells which are maintained at 39° C. It is found that the viability of the white blood cells which normally lasts for about 12 hours is prolonged for up to longer than 24 hours by the addition of the CLA. This extension of the useful life of white blood cells helps prevent their waste.

It will be readily apparent to those skilled in the art that a number of modifications or changes may be made without departing from the spirit and scope of the present invention. Therefore, the invention is only to be limited by the claims.

We claim:

1. A method for the treatment of type I or $I_gE$ mediated hypersensitivity in an animal, said method comprising administering to said animal a therapeutically effective amount of a member selected from the group consisting of a conjugated linoleic acid, an active ester thereof, a non-toxic salt thereof and a mixture thereof.

2. A method of claim 1, in which the hypersensitivity is asthma.

3. A method of alleviating the adverse effects of type I or $I_gE$ mediated hypersensitivity in an animal, said method comprising administering orally or parenterally to said animal a therapeutically effective amount of a member selected from the group consisting of a conjugated linoleic acid, an active ester thereof, a non-toxic salt thereof and a mixture thereof.

4. The method of claim 3 in which at least some of the adverse effects are characteristic of asthma.

5. A method of preserving white blood cells which comprises adding to said white blood cells an amount of CLA which is about 0.1% to about 1% by weight.

6. A method of increasing the white blood cell counts in a mammal comprises administering to said mammal a safe amount of CLA which is effective to increase the white blood cell count in said mammal.

\* \* \* \* \*